United States Patent
Beck et al.

(10) Patent No.: US 7,443,079 B2
(45) Date of Patent: Oct. 28, 2008

(54) METHOD AND APPARATUS FOR CAVITATION THRESHOLD CHARACTERIZATION AND CONTROL

(75) Inventors: Mark J. Beck, Los Gatos, CA (US); Raymond Y. Lillard, Redwood City, CA (US); Eric G. Liebscher, San Jose, CA (US); Frank M. Haidinyak, San Jose, CA (US)

(73) Assignee: Product Systems Incorporated, Campbell, CA (US)

( * ) Notice: Subject to any disclaimer, the term of this patent is extended or adjusted under 35 U.S.C. 154(b) by 190 days.

(21) Appl. No.: 11/228,855

(22) Filed: Sep. 15, 2005

(65) Prior Publication Data

US 2006/0061225 A1    Mar. 23, 2006

Related U.S. Application Data

(60) Provisional application No. 60/610,805, filed on Sep. 17, 2004.

(51) Int. Cl.
*H01L 41/08* (2006.01)
*G01H 3/00* (2006.01)
*G01N 29/00* (2006.01)

(52) U.S. Cl. .................................. 310/328; 73/590
(58) Field of Classification Search ............. 310/328; 73/590
See application file for complete search history.

(56) References Cited

U.S. PATENT DOCUMENTS

| | | | |
|---|---|---|---|
| 3,443,797 A | 5/1969 | Branson | |
| 3,647,387 A | 3/1972 | Benson et al. | |
| 5,367,497 A | 11/1994 | Marschall | |
| 5,436,874 A * | 7/1995 | Kuhn et al. | 367/176 |
| 5,659,173 A * | 8/1997 | Putterman et al. | 250/361 C |
| 5,982,801 A * | 11/1999 | Deak | 372/69 |
| 6,220,472 B1 | 4/2001 | Townsend et al. | |
| 6,655,922 B1 | 12/2003 | Flek | |
| 6,719,449 B1 * | 4/2004 | Laugharn et al. | 366/127 |
| 6,944,097 B1 | 9/2005 | Ferrell | |

(Continued)

FOREIGN PATENT DOCUMENTS

DE    10244387    *    4/2004

(Continued)

OTHER PUBLICATIONS

English translation of German patent DE 10244387 A1 (May 3, 2006).

(Continued)

*Primary Examiner*—Thomas M Dougherty
(74) *Attorney, Agent, or Firm*—Donald J. Pagel

(57) ABSTRACT

An apparatus and method for characterizing cavitation that occurs in a fluid exposed to acoustic energy. The apparatus comprises a vessel for holding the fluid; an acoustic energy generating means for generating acoustic energy, the acoustic energy generating means being positioned to transmit the acoustic energy into the fluid while the fluid is held in the vessel; and a cavitation detection means for detecting cavitation in the fluid held in the vessel. In a preferred embodiment, the cavitation detection means comprises a light detection means, such as a photomultiplier tube, that detects sonoluminescent emission from the fluid. The method comprises the steps of exposing a volume of process fluid to acoustic energy at a specified power level; measuring the photon output from the fluid over a period of time; and when the photon output deviates from a desired level, initiating a remedial step to bring the photon output back to approximately the desired level.

14 Claims, 4 Drawing Sheets

U.S. PATENT DOCUMENTS

| | | | |
|---|---|---|---|
| 7,210,354 B2* | 5/2007 | Puskas | 73/590 |
| 7,273,458 B2* | 9/2007 | Prausnitz et al. | 601/2 |
| 2006/0158956 A1* | 7/2006 | Laugharn et al. | 366/127 |
| 2006/0159552 A1* | 7/2006 | Tessien | 417/53 |
| 2007/0205695 A1* | 9/2007 | Puskas | 310/317 |
| 2007/0262676 A1* | 11/2007 | Madanshetty | 310/311 |

FOREIGN PATENT DOCUMENTS

| | | | |
|---|---|---|---|
| DE | 10244387 A1 | | 4/2004 |
| JP | 11 211664 A1 | | 8/1999 |
| JP | 2000 88638 A1 | | 3/2000 |
| WO | WO 02/05465 A1 | | 1/2002 |
| WO | WO/2002/074021 | * | 9/2002 |

OTHER PUBLICATIONS

J.J. Rosato; M.R. Yalamanchili; M.J. Beck; R.Y. Lillard, "Damage-Free Cleaning of Sub-50 nm Devices Using Directed Megasonics Technology in a Single Wafer Processor" published on Sep. 15, 2004, and presented at the IMEC Conference (Ultra Clean Processing of Silicon Surfaces) in Brussels, Belgium.

Product Systems, Inc., "Prosys Launches the Ultraprobe" Press Release, San Francisco (Jul. 12, 2004).

International Search Report and Written Opinion of the International Searching Authority, PCT/US05/33180, USPTO, Alexandria, VA USA (Mar. 16, 2006).

Young, Ronald F., *Cavitation*, p. 350, Imperial College Press, London, England (1999).

Leighton, T.G., *The Acoustic Bubble*, pp. 492-495, Academic Press, Inc., San Diego, CA USA (1994).

Matula, T.J. and Crum, L.A., "Single-Bubble Sonoluminescence: Some Recent Experiments," *Sonochemistry and Sonoluminescence*, Edited by L.A. Crum, T.J. Mason, J.L. Reisse and K.S. Suslick, pp. 145-158, Kluwer Academic Publishers, Dordrecht, The Netherlands (1999).

Cheeke, J. David N., *Fundamentals and Applications of Ultrasonic Waves*, pp. 380-395, CRC Press LLC, Boca Raton, FL USA (2002).

Gaitan, Dario Felipe, *An Experimental Investigation of Acoustic Cavitation in Gaseous Liquids*, pp. 113-184, Ph.D. Dissertation, UMI, Ann Arbor, MI USA (1990).

Pickworth M. J. W. et al; "Studies of the cavitational effects of clinical ultrasound by sonoluminescence: 2. Thresholds for sonoluminescence from a therapeutic ultrasound beam and the effect of temperature and duty cycle," Physics In Medicine and Biology, vol. 33, No. 11, pp. 1249-1260 (Nov. 1, 1988).

Crum L. A. et al; "Sonoluminescence Produced By Stable Cavitation," Journal of the Acoustical Society of America, vol. 78, No. 1, pp. 137-139 (Jul. 1985).

Stottlemyer T. R. et al; "The effects of surfactant additives on the acoustic and light emissions fro a single stable sonoluminescing bubble," Journal of the Acoutical Society of America, vol. 102, No. 3, pp. 1418-1423 (Sep. 1997).

Asase T. et al; "Observation of Shock Wave Propagation by a Sonoluminescing Bubble," Japanese Journal of Applied Physics, vol. 43, No. 1, pp. 403-404 (Jan. 13, 2004).

Mason, W.; "Extended European Search Report for Application No. EP05798106," European Patent Office, pp. 1-9 (Jan. 21, 2008).

* cited by examiner

METHOD AND APPARATUS FOR CAVITATION THRESHOLD CHARACTERIZATION AND CONTROL

CROSS-REFERENCE TO RELATED APPLICATIONS

This application claims the benefit of priority of U.S. Provisional Patent Application 60/610,805, filed Sep. 17, 2004.

BACKGROUND OF THE INVENTION

1. Technical Field

The present invention relates to technology that uses acoustic energy transmitted through a fluid for cleaning or some other purpose, and more particularly to a system that uses the emission of light from the fluid when it is exposed to the acoustic energy (sonoluminesence) to avoid transient cavitation.

2. Background Information

Historically, many industrial cleaning processes have made use of aqueous chemical fluids to remove particles from objects. In many cases, adding acoustic energy in the frequency range of 1 KHz to 10 MHz into the process bath has been shown to improve the cleaning process by removing particles more completely and in a shorter period of time. Introduction of acoustic energy into plating baths has also been shown to enhance electroplating processes by improved mixing of the chemistry and boundary layer, resulting in fresh species being available at the surface of the object being plated. Additionally, acoustic energy has been shown to help keep the cathode and anode clean.

Acoustically enhanced processes are commonly described as either ultrasonic or megasonic according to the frequency range of the induced sound field. The acoustic energy is commonly generated by exciting a piezoelectric crystal with a sinusoidal AC voltage. The crystal changes dimension at a rate determined by the frequency of the AC voltage. These periodic dimensional changes are mechanical vibrations, the energy from which is coupled into the process fluid through a resonator plate, thus creating an acoustic energy field. The crystal is typically tightly bonded to a transmitting member called a resonator that comes in contact with the fluid.

Ultrasonic cleaning is most appropriate for strong, heat tolerant substrate materials requiring cleaning of objects with moderately complex surface topologies. The ultrasonic frequency range is also well suited for removal of comparatively large particles from these chemically tolerant surfaces. Megasonic cleaning is appropriate for objects with heat and chemical sensitive surfaces, requiring line of sight dependent cleaning. Megasonic cleaning is also the method of choice for cleaning when the particle size is below approximately 0.3 μm.

Acoustic cavitation is generally regarded as the principle mechanism for particle removal in the cleaning process. In an acoustic field, a bubble or cavity is created when the high pressure tears the fluid, creating a bubble or void. These bubbles or voids are called cavities.

These pressure oscillations produce bubbles which expand and contract with the peaks and valleys of the pressure waves. As the bubbles expand and contract, some of the gases which form the bubble are absorbed into the fluid during contraction (compression cycle) and diffuse back into the bubble on expansion (decompression cycle). When the bubble reaches a size that can no longer be sustained by the force of the surface tension of the fluid competing against the force of the pressure differential created by passing acoustic waves, the bubble implodes.

There are two types of acoustic cavitation: stable and transient. In stable cavitation, a stable cavity (or bubble) is mostly gas filled and grows very slowly over many acoustic cycles. The energy released with an implosion event of a stable cavity is much less than that of a transient cavity. In transient cavitation, a transient cavity (or bubble) contains argon gas but has very little or no other gases in it. It will grow to a large size in only a few cycles and releases a much larger amount of energy upon collapse.

Sonoluminescence (SL) is the light released when the bubble collapses or more precisely, implodes. The pressure and speed of the implosion raises the gas inside the bubble to sufficiently high temperatures to cause emission of photons. The light emission from sonoluminescence has a frequency of 200 nm to 600 nm and is generally characterized as being in the UV spectrum.

The sonoluminescence spectrum starts at the roughly the midpoint of the visible light spectrum and extends well into the UV range. It occurs principally due to the presence of naturally occurring argon which is dissolved in the water. It is argon which is the major component in the plasma that is critical to the photon emission at the time of implosion. As cavities oscillate in size, the mostly gaseous nitrogen and oxygen molecules move back and forth in and out of the bubble with each pressure cycle change. Argon however does not, and consequently the concentration of argon inside the bubble begins to dramatically rise above the naturally occurring level of about 1% found in the earth's atmosphere. Therefore, when the bubble collapses, the predominant gas in the bubble is argon, and it is argon (and the other Noble gases) which primarily exhibit the property of sonoluminescence. Historically, sonoluminescence has been associated with transient cavitation, and was not thought to occur in stable cavitation.

The cavitation threshold is the point at which cavitation becomes predominately transient and the cavities begin to collapse violently emitting a high level of energy in the form of photons. In the past, sensors that detect sound pressure, known as hydrophones, have been used to detect transient cavitation because transient cavitation implosion events emit sufficient sound energy above the intrinsic detection threshold of the sensor. However, stable cavitation implosions emit far less energy, and are therefore undetectable by hydrophones, for practical purposes.

Another way to measure cavitation is through the use of cavitation cells, such as those described in the published Patent Cooperation Treaty document WO 02/05465 A1. Cavitation cells are used to sense fluid cavitation output directly in the cleaning bath, and are valuable tools for gathering general information on how well a bath is working or how one cleaning bath compares to another.

However, cavitation cells suffer from several problems. For example, cavitation cells cannot be left in the process bath during operation because the probe needs to be in the energy field to make its measurements and the object being cleaned also needs to be in the field. Additionally, the cell geometry does not guarantee that the fluid properties inside the cell are the same as what is in the tank, and gas buildup inside the cell affects data reproducibility.

In the early 1990's, scientists performed tests on a single bubble suspended in a fluid and determined that the oscillating bubble did emit photons at every negative pressure cycle. This was called SBSL for Single Bubble Sonoluminescence. It was theorized and confirmed that a sound field of many bubbles may have the same light synchronized response to the negative pressure cycles as a single bubble. This phenomenon became known as MBSL (Multi-Bubble Sonoluminescence) and is the dominant condition found in the tanks of most acoustically enhanced cleaning systems. The MBSL photon emission spectrum has since been measured and found to be similar to that of SBSL for similar fluid properties and conditions.

A collapsing bubble in close proximity to the surface of a sensitive substrate can exert very high localized pressure and temperatures, causing structural damage to the substrate. Cavitation implosions have been shown to have the energy of 50-150 atmospheres of pressure and temperatures of 5,500 degrees Kelvin. Exposure to the energy released by cavitation implosion events is known to be the primary mechanism for the erosion damage to the surfaces of sensitive and finely structured devices. Cleaning processes have been developed which achieve reasonably high yield rates with acceptably low damage rates. However, these processes lack real-time feedback to enable closed loop control of conditions in the cleaning tank based on cavitation level.

Recent cleaning processes have been developed that have such a low power or high frequency that commercial suppliers of the cleaning equipment have advertised them as having no cavitation. What is needed is technology that can characterize these low power cleaning processes and use them to prevent or mitigate the damage caused by transient cavitation.

SUMMARY OF THE PRESENT INVENTION

Briefly, the present invention is a method and apparatus for characterizing the cavitation properties of fluids by observing the intensity of photon emission during sonoluminescence. In the present invention, it is shown that photon emission is occurring in low power acoustic energy cleaning processes. It is thought that this photon emission is from stable cavitation and that the stable cavitation is multibubble sonoluminescence (MBSL).

In preferred embodiments, the method and apparatus of the present invention measure photon emissions in the presence of stable cavitation. The photon emission information is used in a feedback loop to mitigate surface damage to delicate substrates by controlling the power level of the AC voltage signal applied the acoustic transducer in the production tank. Pressure changes in the fluid can also be used as a measure of cavitation.

An apparatus that allows utilization of this method comprises a vessel through which a process fluid flows; an acoustic energy generating means for generating acoustic energy and transmitting the acoustic energy into the fluid while the fluid flows through the vessel; and a cavitation detection means, such as a photomultiplier tube or a hydrophone, for detecting and/or quantifying cavitation in the fluid in the vessel induced by the acoustic energy.

The method of the present invention comprises the steps of: exposing a volume of process fluid to acoustic energy at a specified power level; measuring the photon output from the fluid at the specified power level over a period of time; determining a desired level of photon output; and, when the photon output deviates from the desired level, adjusting a process parameter to bring the photon output back to the desired level.

In research applications, the present invention is used to study the effects of physical parameters such as temperature, chemical composition or concentration, dissolved gas concentration, atmospheric pressure and the intensity of the acoustic energy field, on the cavitation properties of sonochemical fluids. The cavitation properties can then be correlated to surface damage, plating efficiency or the general efficacy of other sonochemical processes.

In commercial applications, the invention is used in acoustically enhanced chemical cleaning or other sonochemical processes, such as plating. In the cleaning case, this information is used to reduce chemical consumption by eliminating premature bath changes and prevent overdue bath changes from causing reduced PRE (particle removal efficiency) and the resulting loss of product due to particle compromised structures. The invention also allows adjustments to be made that avoid the damaging effects of transient cavitation.

DETAILED DESCRIPTION OF THE INVENTION

Figure 1:
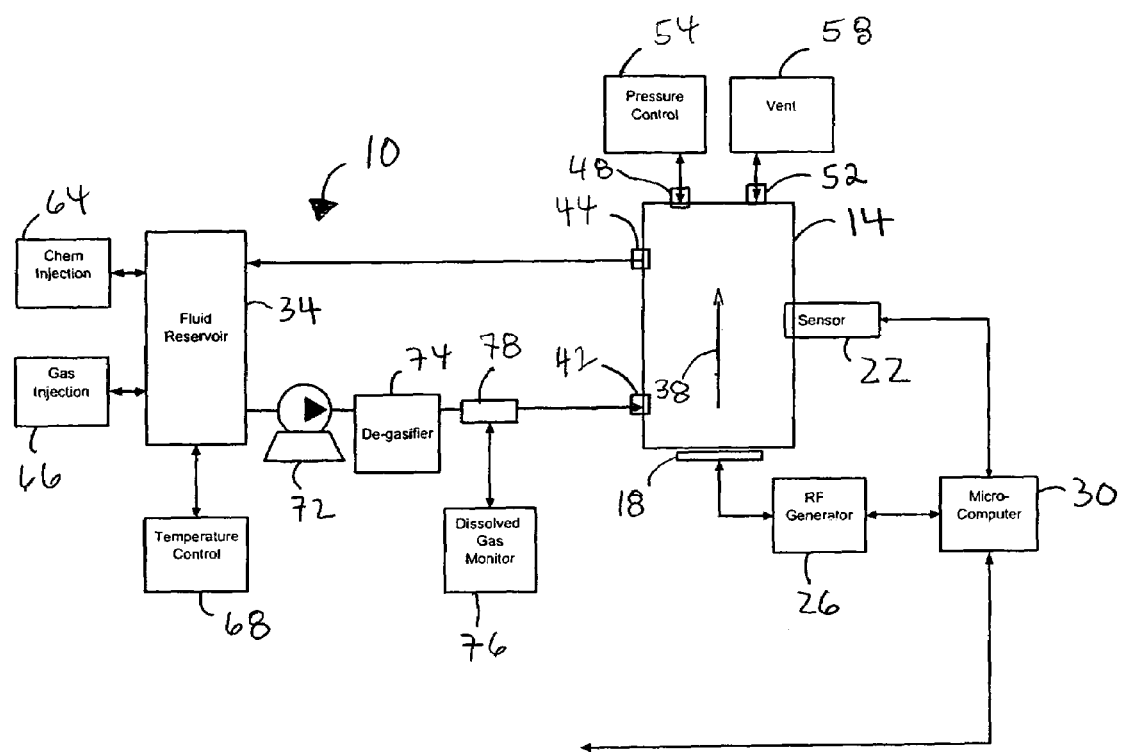
FIG. 1 is a schematic view of a cavitation characterization system according to the present invention.

FIG. 1 illustrates a cavitation characterization system 10 comprised of a cavitation cell 14, an acoustic transducer 18 and a sensor 22. A power supply 26, such as a radio frequency (RF) generator, supplies power to the transducer 18. A microcomputer 30 controls the power supply 26 and collects data from the sensor 22. A fluid reservoir 34 provides a supply of a process fluid to the cell 14.

The cavitation cell 14 is a small light-tight chamber through which process fluids are caused to flow, usually in the direction of the arrow 38. Thus, the inside of the cell 14 contains a representative sample of the process fluid which is caused to cavitate by an acoustic field supplied by the transducer 18. The process fluid may be from a nearby tank, such as the fluid reservoir 34 in a research application, or it may be a sample of process fluid from a tank in production process equipment. The cell 14 must be sufficiently light-tight so as to allow detection of photon emission levels as low as tens of photon counts per second. Additionally, the cell should remain dark even when not being used to avoid damaging the sensor 22, or increasing the background noise in the sensor 22.

The cell 14 may have a multiplicity of ports to enable management or control of the fluid test parameters as desired for a specific application or test regimen. These ports include, but are not limited, to an inlet port 42 and an outlet port 44 for allowing the process fluid sample to flow through the cell 14, as well as a pressure control port 48 to control atmospheric (barometric) pressure above the surface of the process fluid, and a vent control port 52 to remove gases which may gather at the top of the cell 14. Additional ports may be used, for example to enable fluid level control in the cell 14, or to accommodate sensors to measure various other process fluid characteristics. The need to correlate measurements of fluid properties to the photonic emission level is implicit to the purpose of the invention.

In the preferred embodiment, the power supply 26 shown in FIG. 1 is an electrical power generator capable of delivering sinusoidal electrical energy at power levels and at frequencies which are appropriate for the specific process that is being monitored. Thus the power supply 26 and the acoustic transducer 18 are designed to be compatible with the process being observed. In a representative example, the frequency of operation of the power supply 26 may be near one megahertz (1 MHz). A 1000 watt RF generator capable of generating RF voltages in the frequency range of 0.4 to 2.0 megahertz may function as the power supply 26. However, the system 10 can be used at any frequency or power level where acoustic cavitation is observed or monitored in a fluid, including in the 2.0 to 5.0 or higher megahertz range, so many types of power supply 26 can be used.

In operation, the crystal 116 (shown in FIG. 2) is excited by the sinusoidal AC voltage from the power supply 26, which causes it to expand and contract sympathetically with the driving AC voltage. These dimensional changes are mechanical energy which is coupled by a resonator 118 into the process fluid in the cavity 84. This coupling gives rise to an acoustic sound field in the process fluid. Other acoustic energy generating devices and designs may be used to supply acoustic energy to the process fluid. Other embodiments may employ different means such as electromagnetic fields and or other mechanical means to create an acoustic field. Additionally, multiple transducers may be employed and operated independently or in concert.

A microcomputer 30 functions as a computer means for collecting data from the sensor 22 about the light emitted from the fluid. The microcomputer 30 is also used to control the intensity of the acoustic field inside the cell 14, by controlling the energy (electrical or otherwise) applied by the power supply 26 to the transducer 18 or other energy coupling arrangement. Typically, the photon emission level is measured by the sensor 22 at various levels of acoustic energy, and this data is collected by the microcomputer 30. Analysis of the data by the microcomputer 30 allows quantitative and qualitative information to be outputted from the microcomputer 30, for example in the graphical format shown in FIG. 3. In a prototype system, a commercially available laptop computer with a Pentium® microprocessor was used as the microcomputer 30, but many other types of computing devices, including embedded microprocessors, can be used for this purpose.

The fluid reservoir 34 is a vessel containing the process fluid to be observed. It is where most of the physical and chemical parameters are controlled. Chemicals (in solid, liquid or gaseous phases) may be metered into the bath as desired. In research applications, this is merely a place to store and condition the fluid whose cavitation behavior is being studied. In a production application this element is the actual cleaning tank where process parameters are actively being monitored and adjusted by the information fed back from the invention. This vessel may be open of closed. If the cell is being used to study fluids at pressures other than 1 atmosphere, the reservoir may need to be closed and pressurized as well.

In practice, different process fluids are used for different processing tasks. The exact composition of many process fluids is proprietary to the companies that manufacture the fluids. However, typical process fluids include deionized and/or distilled water, aqueous solutions of ammonium hydroxide, hydrogen peroxide, hydrochloric acid, nitric acid, acetic acid, hydrofluoric acid, and combinations of these reagents. Commonly used process fluid compositions are referred to as SC-1 and SC-2.

A chemical injection block 64 indicates an optional chemical delivery system used to maintain a proscribed chemical composition of the process fluid. For example, the concentration of ammonium hydroxide or hydrogen peroxide in the process fluid can be replenished through block 64. Similarly, a gas injection block 66 indicates an optional gas injection system to increase the level of dissolved gases in the process fluid. For example, the concentration of oxygen in the process fluid can be replenished through block 66.

A temperature control block 68 indicates an optional temperature control system for controlling the temperature of the process fluid in the reservoir 34. A pump 72 is a suitably chosen pump to cause process fluid to flow through the cell 14 and other components of the system 10. A degasifier 74 is an optional device which can remove dissolved gases, like ambient air, from the process fluid. A dissolved gas monitor 76 is an optional device which can measure the level of a dissolved gas like oxygen or argon in the process fluid at a sampling station 78.

The pressure control block 54 is an optional device that controls the barometric pressure applied to the surface of the process fluid. This may include a pressure regulator to apply a positive pressure or a vacuum pump and regulator to apply negative pressure. It is recognized that use operation at pressures other than 1 atmosphere may have influence on pumping and other fluid handling issues outside the scope of this invention. It is implicit that the design of the cell 14 and sensor 22 may need special treatment when non-atmospheric pressures are present. The vent port 58 and associated equipment may be used to any out-gassing products if necessary. This port may also be used for level detection and control.

Figure 2:
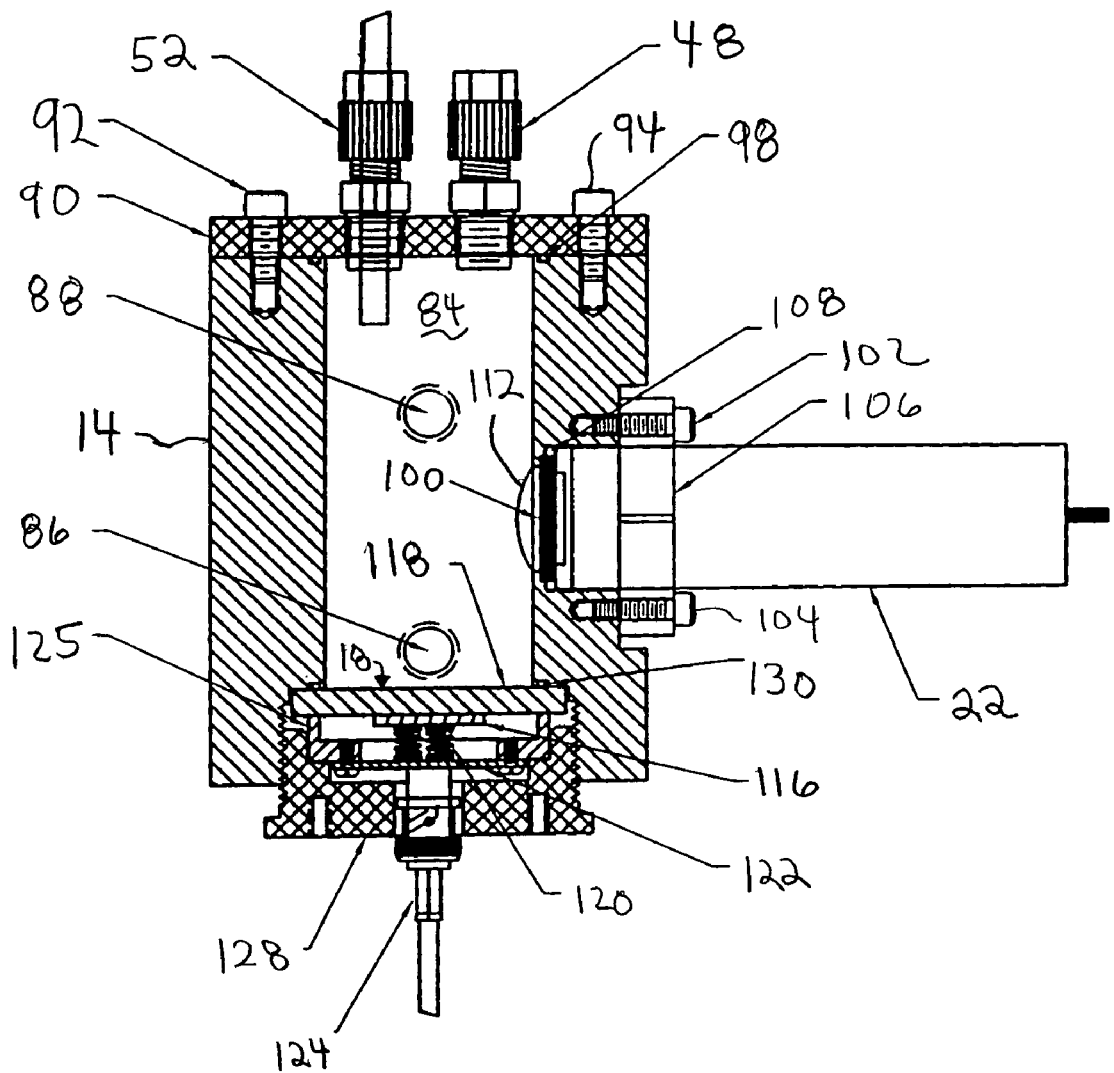
FIG. 2 is a cross-sectional view of a cavitation cell according to the present invention.

FIG. 2 illustrates the cell 14 in more detail. FIG. 2 is a cross-sectional view of a hollow cylindrically shaped cell 14. The cell 14 must be light-tight and fluid-tight. A cavity 84 is the space inside of the hollow cell 14, and the process fluid flows through the cavity 84. A lower aperture 86 is a hole that accepts a fitting to form the inlet port 42 through which the process fluid enters the cavity 84. An upper aperture 88 is a hole that accepts a fitting to form the outlet port 44 through which the process fluid exits the cavity 84 and the cell 14. A top end cover 90 is held in place by a pair of screws 92 and 94, and an O-ring 98 ensures that the cover 90 makes a fluid tight seal.

The sensor 22 is a light detection means for detecting light emitted from the fluid held in the cell 14 when cavitation is occurring (i.e. sonoluminescence). In the preferred embodiment, the sensor 22 is a photomultiplier tube (PMT), capable of sensing very low levels of photon emission, (on the order of 100 photon counts per second). For example, the photomultiplier tube model number P25232, available from Electron Tubes Inc. of Rockaway, N.J. may be used as the sensor 22. The photomultiplier tube has a window 100 through which light enters the photomultiplier tube. Preferably, the photomultiplier tube is purchased with the window 100 comprising a material that allows ultraviolet (UV) radiation to enter the photomultiplier tube.

The photomultiplier tube (sensor 22) is positioned in an aperture in the cell 14 and is held in place by a pair of screws 102 and 104 and a mounting ring 106. An O-ring 108 ensures that the sensor 22 makes a fluid tight seal. A lens cover 112 is positioned over the window 100 to protect the window 100 from chemical interaction with the process fluid. In the preferred embodiment, the lens cover 112 comprises optical grade synthetic sapphire that allows ultraviolet radiation to enter the photomultiplier tube, but other materials can be used.

In addition to the sensor 22, other sensors may be included in the system 10. For example, lasers may be added to observe light scattering when cavitation bubbles are present, even when photon emission is not. Other sensing devices, such as a hydrophone, may also be added to the cell 14 to enable correlation of data from a multiplicity of sensors. A CCD array could also be used to image the sonoluminescence effect, and would be used with a laser to detect light scattering by cavitation bubbles.

The acoustic transducer 18 an acoustic energy generating means for generating acoustic energy. In the preferred embodiment, this is an acoustic transducer which converts electrical energy into acoustic (or sound) waves in the process fluid contained in the cell 14. In the preferred embodiment, the transducer 18 comprises a piezoelectric crystal 116, comprised of a material such as PZT (Lead Zirconate Titanate), that is bonded to a resonator 118. A pair of spring electrical connectors 120 and a printed circuit board 122, provide electrical connections to the power supply 26 via an RF power connection cable 124, for example as is disclosed in U.S. Pat. No. 6,431,908. A ground contact/clamp ring 125 supports the resonator 118.

In the preferred embodiment, the crystal 116 is attached to the resonator 118 using indium, as is disclosed in U.S. Pat. Nos. 6,722,379, 6,188,162 and 6,222,305, and the resonator 118 comprises a chemically inert material such aluminum or stainless steel coated with the fluorinated polymer perfluoroalkoxy (PFA). However, other means of attachment for the resonator 118 and crystal 116 can be used, such as the epoxy bonded crystals disclosed in U.S. Pat. No. 4,804,007.

The sensor 18 is mounted on a bottom end cover 128, which fits into the cell 14 but which is detachable from the cell 14 for service. An O-ring 130 ensures that the cover 128 makes a fluid tight seal. When the cover 128 is mounted in place, the resonator 118 is in direct contact with the process fluid. In alternate embodiments, the crystal 116 can be bonded to a side-wall of the cell 14.

In a preferred embodiment, the cell 14 is cylindrical in shape and is comprised of a material that is both light-tight and impervious to chemical reaction with the process fluid. For example, a metal such as stainless steel or aluminum in which all surfaces that come into contact with the process fluid have been coated with a chemically inert substance like the fluorinated polymer perfluoroalkoxy (PFA) can be used as the cell 14. Other chemically inert materials that can function as the coating include the fluorinated polymers polytetrafluoroethylene (PTFE), fluorinated ethylene-propylene (FEP), or tetrafluoroethylene (TFE) and other formulations, including the materials that are marketed under the trademark Teflon™; the fluorinated polymer ethylene chlorotrifluoroethylene (ECTFE), including the material marketed under the trademark Halar™; or the fluorinated polymer polyvinylidene fluoride (PVDF), including the material marketed under the trademark Kynar™. Similarly, the resonator 118 can be coated with these chemically inert materials.

Certain applications are likely to require alternate physical shapes of the cavity 84 inside the cell 14, and/or other internal structures in the cell cavity to manage the flow of acoustic energy within the cell 14. This could involve tilting the cell 14 such that the surface of the process fluid is not parallel to the face of the transducer 18, thereby forcing the acoustic reflections from the surface of the fluid to not reflect directly back to the transducer. It is desirable under certain conditions that acoustic wave absorbing material can be used to dampen or kill standing waves. Other embodiments require internal shapes and structure to create standing acoustic waves.

In an alternate configuration, the cell 14 may be essentially inverted from the configuration shown in FIG. 1. Driving the acoustic field downward against the forces of gravity and fluid pressure allows observation of bubbles in alternate conditions. Laterally oriented configurations are also possible.

Figure 3:
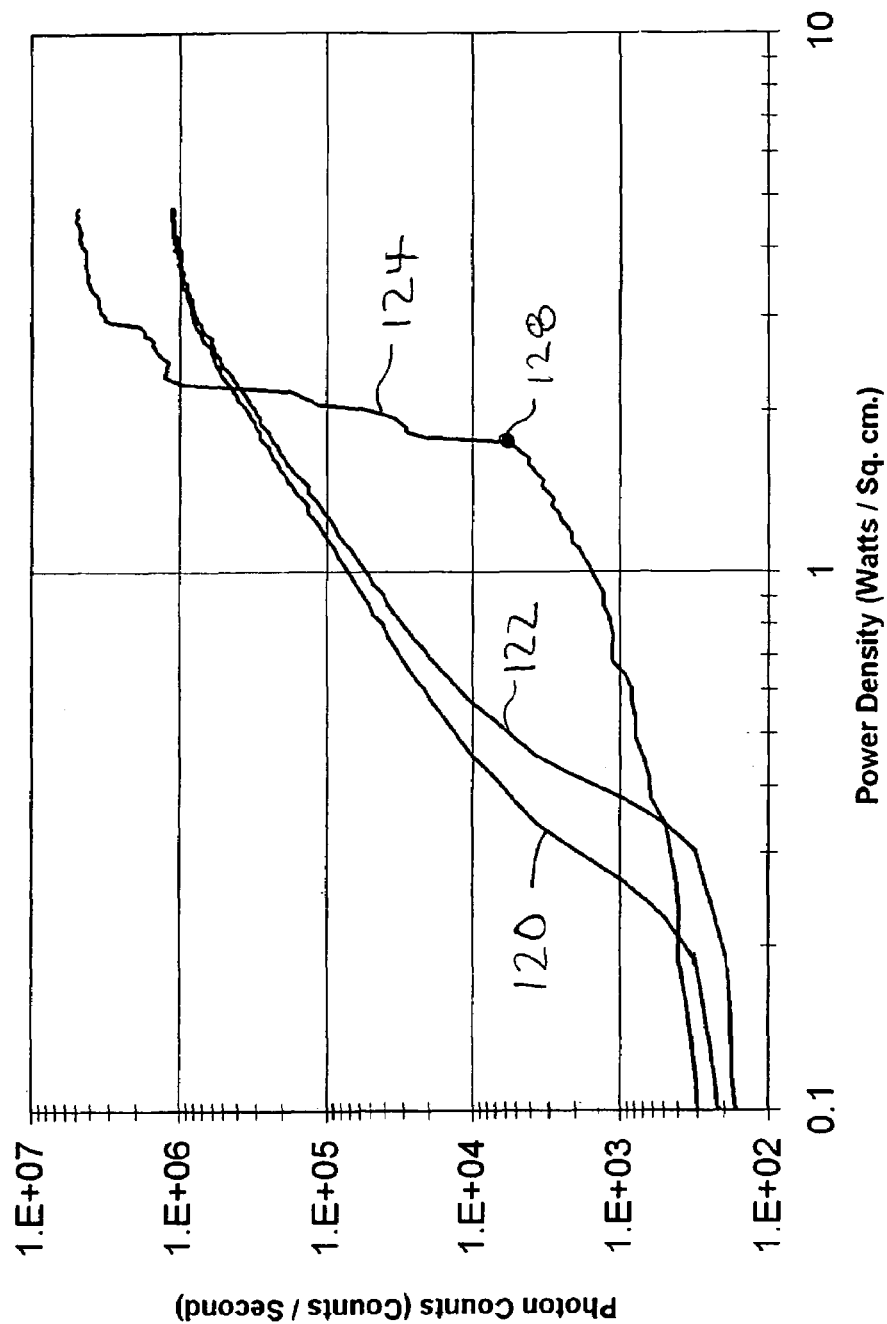
FIG. 3 is a graph of photon count versus power density for three different process fluids according to the present invention.

FIG. 3 illustrates one type of data obtained from the system 10. FIG. 3 is a graph on log-log paper of photon count versus power density for three different process fluid situations. Line 120 illustrates the sonoluminescent behavior of deionized water when the power supply 26 provides an AC voltage at a frequency of one megahertz. Line 122 illustrates the sonoluminescent behavior of deionized water when the power supply 26 provides an AC voltage at a frequency of two megahertz. Line 124 illustrates the sonoluminescent behavior of SC1 process fluid (a solution of deionized water, hydrogen peroxide and ammonium hydroxide in a 100:2:1 ratio) when the power supply 26 provides an AC voltage at a frequency of one megahertz.

FIG. 3 illustrates several important features regarding the characterization of cavitation in fluids. First, on line 124, a region centered around the power density of approximately 2.0 watts/cm$^2$, shows a rapid increase in the light output from the process fluid. A point 128 at the approximate base of the region of rapid increase in the light output (approximately 1.9 watts/cm$^2$), is taken to indicate the point at which cavitation in the process fluid has become predominantly transient (i.e., point 128 represents the cavitation threshold). As was explained previously, this is because the violent collapse of cavities in the process fluid during transient cavitation is known to emit a high level of energy in the form of photons. Thus, the region to the right of point 128 is thought to represent a region of transient cavitation, while the region to the left of point 128 is thought to represent a region of stable cavitation. The observation that measurable amounts of photons are emitted by fluids during stable cavitation (at least in the multi-bubble regime) has not previously been reported, and the present invention appears to be the first commercially useful application of this phenomena. The observation that stable cavitation is occurring in this power region also appears to be new.

Figure 4:
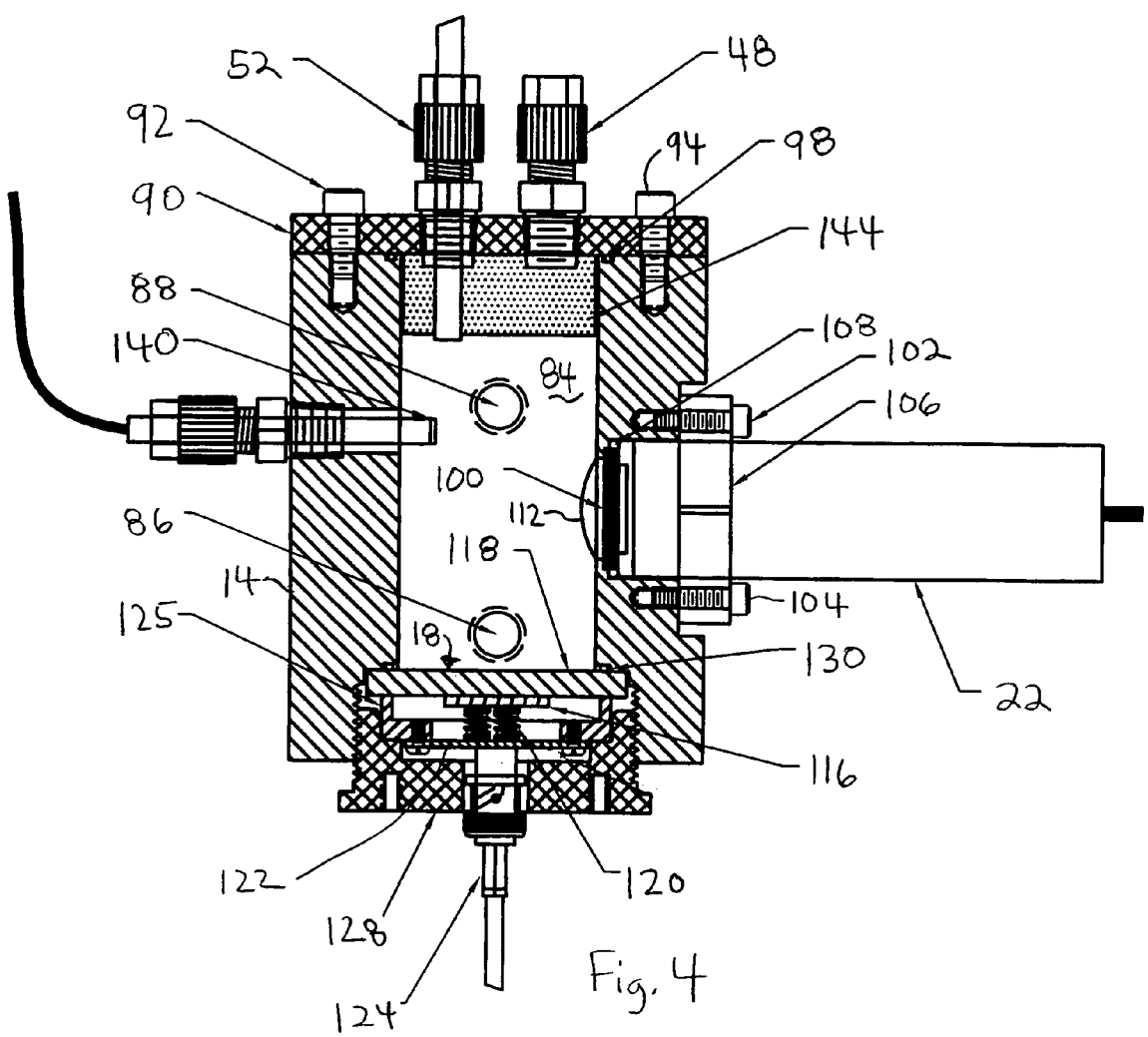
FIG. 4 is a cross-sectional view of and alternative embodiment of the cavitation cell according to the present invention.

FIG. 4 illustrates an alternative embodiment of the cell 14 shown in FIG. 2. Elements in FIG. 4 that are identical to the corresponding elements in FIG. 2 are indicated by the same reference numerals. In FIG. 4, a hydrophone 140 and an acoustic baffle 144 have been added to the cell 14.

The hydrophone 140 provides a means for measuring the pressure in the fluid contained in the cavity 84 as the power is increased in steps. The pressure readings from the hydrophone 140 are used to confirm that the ultraviolet light output being measured at very low power inputs is occurring during a period of very low pressure in the fluid, thus indicating that stable cavitation exists.

The baffle 144 is used to absorb acoustic energy (sound) at the top of the cell 14, thereby preventing or reducing reflected acoustic waves. In a normal acoustic energy cleaning system, the sound energy is traveling at 1.5 km/sec so it bounces around the tank very quickly. Most areas of such a tank are exposed to both the original sound energy generated by the acoustic transducer and to reflections of acoustic waves. It is necessary to understand the SL light output of a fluid under these conditions, so a cell operating without the baffle 144 (FIG. 2) mimics this.

However, in some cases, it is desirable to study exactly how the fluid will react to sound. In such cases, the cell 14 must also provide an environment that allows a pure single pass of sound energy wave to be studied (i.e. without acoustic reflections). The baffle 144 (FIG. 4) absorbs the sound at the end of the cell and does not allow for reflections. This single pass sound exposure to the fluid has a different output of SL light result.

Returning to FIG. 3, use of FIG. 3 allows conditions to be selected for SC1 process fluid that will keep cavitation in the process fluid below the cavitation threshold. For example, keeping the power density below approximately 1.9 watts/ cm² will keep cavitation in the stable cavitation region. This is desirable, for example, in situations where it is known that the energy released during transient cavitation would damage the article being cleaned or otherwise processed by the process fluid, or where transient cavitation is undesirable for some other reason. The lines 120 and 122 have shapes that are similar to line 124, although the regions of rapid increase in the light output for these two fluids, under the given conditions, are slightly shifted. A comparison of line 120 to line 122 indicates that the frequency of the power supply has an effect on the cavitation properties of the fluids.

The sonoluminescent behavior of process fluids displayed in FIG. 3 provides a method for controlling the cavitation in a fluid; and specifically, for ensuring that the process fluid stays in the stable cavitation state as opposed to the transient cavitation state. The method comprises the steps of:
 a) exposing a volume of process fluid to acoustic energy at a specified power level;
 b) measuring the photon output from the fluid over a period of time; and
 c) when the photon output deviates from a desired level, initiating a remedial step to bring the photon output back to approximately the desired level.

This process can be carried out using the cell 14 shown in FIGS. 1 and 2. In an initial procedure, a graph like FIG. 3 is developed for a particular process fluid and the conditions that yield a desired level of stable cavitation are noted. For example, in FIG. 3, the conditions at the power density of one watt/cm² might be selected for SC1 process fluid. At this point, the photon count is about 1500 counts/second, so this would be the desired photon output for the method.

Conditions in an acoustic energy processing tank on a production line using SC1 process fluid are set to the previously determined level ((e.g. the acoustic transducer in a semiconductor wafer cleaning tank is driven at one watt/cm²). Then, a continuous stream of the SC1 process fluid from the acoustic energy processing tank is allowed to enter the cell 14 through the port 42. The process fluid flows through the cavity 84 and out the port 44 while the transducer 18 transmits acoustic energy into the flowing process fluid. The resulting light emission from the process fluid is monitored by the sensor 22. If the light output varies from the level of approximately 1500 counts/second, an alarm is given and remedial steps are taken.

The remedial step could be to simply stop the process. Alternatively, a process parameter could be varied in an attempt to force the cavitation condition (as indicated by the photon count) back to the desired level. The process parameter could be any relevant process parameter, including the parameters discussed previously with respect to FIG. 1. These are changing the gas concentration in the process fluid (using the gas injection block 66), changing the temperature of the process fluid (using the temperature control 68), or changing the chemical compensation of the process fluid (using the chemical injection block 64). Alternatively, the frequency or the power output of the power supply 26 could be varied.

An apparatus that allows utilization of this method comprises a vessel, such as a light tight vessel, for holding a fluid (the cell 14); an acoustic energy generating means for generating acoustic energy (the transducer 18), the acoustic energy generating means being positioned to transmit the acoustic energy into the fluid while the fluid is held in the vessel; and a cavitation detection means (the sensor 22) for detecting and/or quantifying cavitation (i.e. for measuring cavitation) in the fluid held in the vessel when cavitation is induced in the fluid by the acoustic energy. In a preferred embodiment, the cavitation detection means comprises a light detection means, such as a photomultiplier tube. However, in other embodiments, pressure changes in the fluid can be used to measure (detect and/or quantify) cavitation in the fluid, so the hydrophone 140, or some other means, can function as the cavitation detection means.

Additional features that can be added to the apparatus include a power generation means (the power supply 26) for supplying variable amounts of power to the acoustic energy generating means; the computer means (the computer 30) for collecting data from the light detection means about the light emitted from the fluid; the chemical injection block 64; the gas injection block 66; the temperature control 68; and the dissolved gas monitor 76. Still other features include fluid injection means for injecting fluid into the vessel (the pump 72), the gas monitoring means associated with the fluid injection means for measuring a concentration of one or more gasses dissolved in the fluid (the gas monitor 76), and the temperature control means for controlling the temperature of the fluid (the temperature control 68).

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true scope of the invention.

We claim:

1. An apparatus for characterizing cavitation in fluids comprising:
 a light-tight vessel through which a fluid can flow;
 an inlet port positioned in the light-tight vessel for allowing the fluid to enter the light-tight vessel;
 an outlet port positioned in the light-tight vessel for allowing, the fluid to flow out of the light-tight vessel;
 an acoustic energy generating means for generating acoustic energy, the acoustic energy generating means being positioned to transmit the acoustic energy into the fluid when the fluid flows through the light-tight vessel; and
 a light detection means for detecting and/or quantifying light emitted from the fluid when the fluid flows through the light-tight vessel and when cavitation is induced in the fluid by the acoustic energy.

2. The apparatus of claim 1 wherein the light-tight vessel is sufficiently light-tight to allow the detection of photon emission levels as low as tens of photon counts per second.

3. The apparatus of claim 1 wherein the light detection means comprises a photomultiplier tube.

4. The apparatus of claim 1 further comprising a pressure measuring means for measuring pressure in the fluid.

5. The apparatus of claim 4 wherein the pressure measuring means comprises a hydrophone.

6. An apparatus for characterizing cavitation in fluids comprising:
 a light-tight vessel through which a fluid can flow, the light-tight vessel being sufficiently light-tight to allow the detection of photon emission levels as low as tens of photon counts per second;
 an inlet port positioned in the light-tight vessel for allowing the fluid to enter the light-tight vessel;
 an outlet port positioned in the light-tight vessel for allowing the fluid to flow out of the light-tight vessel;
 an acoustic energy generating means for generating acoustic energy, the acoustic energy generating means being positioned to transmit the acoustic energy into the fluid when the fluid flows through the light-tight vessel; and a light detection means for detecting sonoluminescent light emitted from the fluid when the fluid flows through the light-tight vessel and when cavitation is induced in the fluid by the acoustic energy.

7. The apparatus of claim 6 wherein the acoustic energy generating means comprises a piezoelectric crystal.

8. The apparatus of claim 6 wherein the light detection means comprises a photomultiplier tube.

9. The apparatus of claim 6 further comprising a pressure detection means.

10. The apparatus of claim 9 wherein the pressure detection means comprises a hydrophone.

11. The apparatus of claim 6 further comprising a baffle means for absorbing acoustic energy.

12. The apparatus of claim 6 further comprising:
power generation means for supplying variable amounts of power to the acoustic energy generating means; and
computer means for collecting data from the light detection means about the light emitted from the fluid.

13. The apparatus of claim 6 further comprising:
fluid injection means for injecting fluid into the light-tight vessel; and
gas monitoring means associated with the fluid injection means for measuring a concentration of one or more gasses dissolved in the fluid.

14. The apparatus of claim 6 further comprising:
temperature control means for controlling the temperature of the fluid.

\* \* \* \* \*